United States Patent [19]

Marrelli

[11] Patent Number: 4,977,915

[45] Date of Patent: Dec. 18, 1990

[54] DEMULSIFIER CONTROL SYSTEM AND METHOD

[75] Inventor: John D. Marrelli, Houston, Tex.

[73] Assignee: Texaco Inc., White Plains, N.Y.

[21] Appl. No.: 433,104

[22] Filed: Nov. 8, 1989

[51] Int. Cl.$^5$ .................... G01N 33/26; B01D 17/05
[52] U.S. Cl. ........................................ 137/4; 137/91
[58] Field of Search ............... 137/4, 91, 92, 3, 88; 73/61.1 R

[56] References Cited

U.S. PATENT DOCUMENTS

| | | | |
|---|---|---|---|
| 4,200,550 | 4/1980 | Scherrer | 137/4 X |
| 4,266,188 | 5/1981 | Thompson | 73/61.1 R |
| 4,401,575 | 8/1983 | Stewart | 137/61.1 R |
| 4,548,226 | 10/1985 | Iino | 137/91 |
| 4,660,414 | 4/1987 | Hatton | 137/61.1 R |
| 4,776,210 | 10/1988 | Baillie | 137/61.1 R |
| 4,873,648 | 10/1989 | Mouser | 73/61.1 R X |

Primary Examiner—Alan Cohan
Attorney, Agent, or Firm—Robert A. Kulason; James J. O'Loughlin; Ronald G. Gillespie

[57] ABSTRACT

The present invention controls the addition of a demulsifier through a petroleum stream by causing the petroleum stream to have a density gradient relating to its water content. The petroleum stream is sampled at two different locations along the density gradient to provide two sample streams. The watercut of each sample stream is determined and at least one single correspondent to the determination has provided. The demulsifier from a source is controlled in accordance with the watercut determinations and provided to the petroleum stream prior to the creation of the density gradient.

17 Claims, 3 Drawing Sheets 4,977,915

DEMULSIFIER CONTROL SYSTEM AND METHOD

BACKGROUND OF THE INVENTION

1. Field of the Invention

The present invention relates to control systems and methods in general and, more particularly, a control system method for controlling demulsifier entering a petroleum stream.

SUMMARY OF THE INVENTION

The present invention controls the addition of a demulsifier through a petroleum stream by causing the petroleum stream to have a density gradient relating to its water content. The petroleum stream is sampled at two different locations along the density gradient to provide two sample streams. The watercut of each sample stream is determined and at least one single correspondent to the determination has provided. The demulsifier from a source is controlled in accordance with the watercut determinations and provided to the petroleum stream prior to the creation of the density gradient.

The object and advantages will appear more fully hereinafter, from a consideration of the detailed description that follows, taken together with the accompanying drawings where one embodiment is illustrated by way of example. It is to be expressly understood, however, that the drawings are for illustrated purposes only, and are not to be construed as defining the limits of the invention.

DESCRIPTIONS OF THE DRAWINGS

FIG. 1 in partial scamatic form and in partial simplified block diagram form, shows a demulsifier control system constructed in accordance with the present invention.

DESCRIPTION OF THE INVENTION

Figure 1:
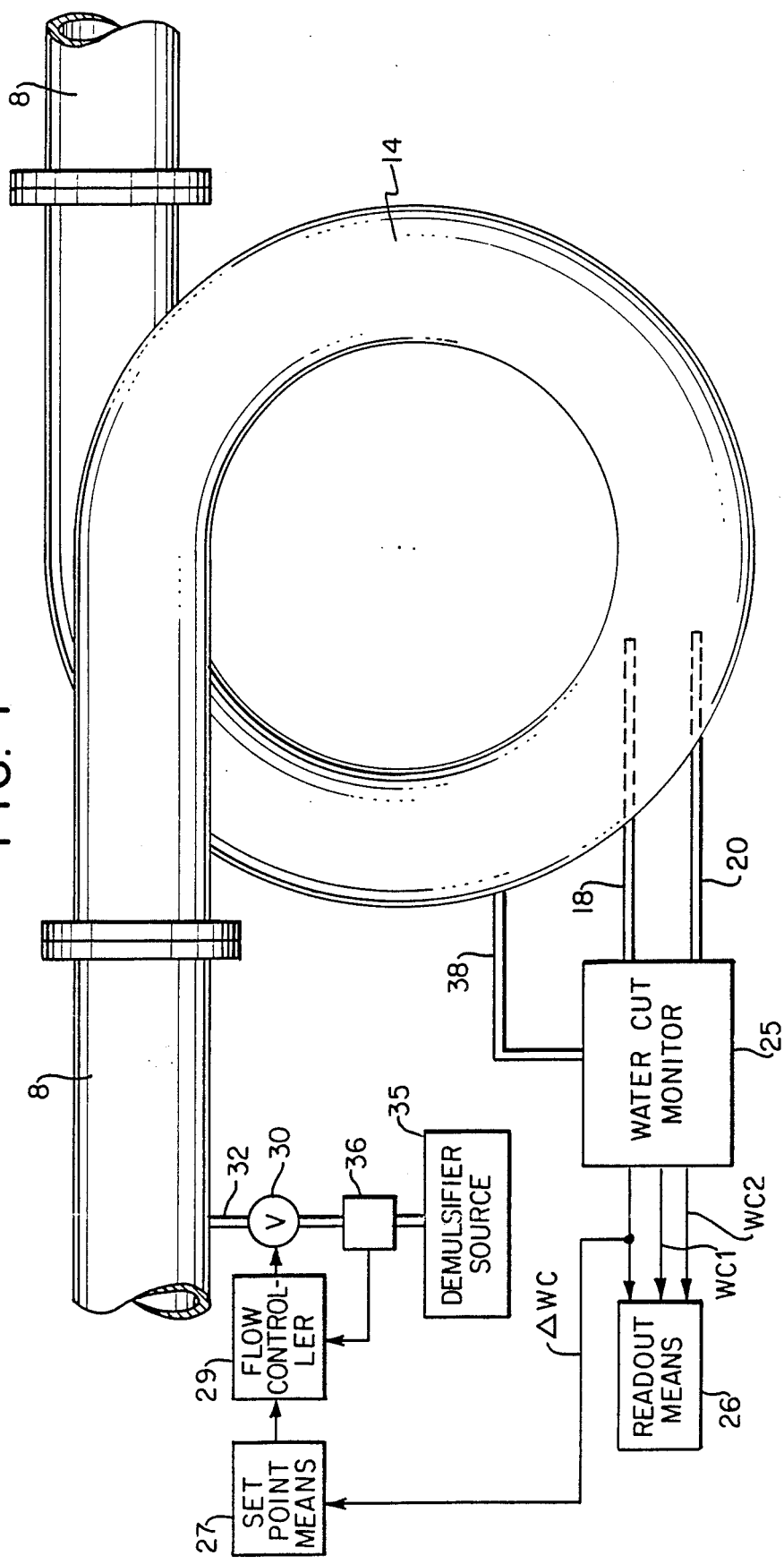

With reference to FIG. 1 there is shown a pipeline 8 carrying a petroleum stream which has a centrifugal loop 14 connected to it, whose output again is connected to pipeline 8. The petroleum stream in essence, while it is being carried by pipeline 8 is submitted to centrifugal forces by centrifugal loop 14 causing the petroleum stream to tend to stratify by density. Thus the heavier water rich portions tend to move to the outer edge of loop 14, while the oil rich layer tend to move to the inner edge of loop 14, thus establishing a density gradient. While the petroleum stream is being centrifuged, sampling tubes 18 and 20 remove sample streams of the inner oil rich layer and the outer water rich layer, respectively, and provides them to a watercut monitor 25. Water cut monitor 25 determines the watercuts of both sample streams and provides signals WC1, WC2 and Δ WC corresponding to the watercut of one sample stream, the watercut of the other sample stream and the difference between the two watercuts, respectively. Water cut monitor 25 provides signals WC1, WC2 and Δ WC to read out means 36. Read out means provides a read out of signals WC1, WC2 and Δ WC as well as a record. Signal Δ WC is provided to set point means 27.

Signal Δ WC controls the addition of the demulsifier to pipeline 8 through a line 33. Set point means 27, in response to signal Δ WC, provides a signal to a flow controller 29. Flow controller 29 provides a control signal to a valve 30 in a line 32. Line 32 is connected to pipeline 8 prior to centrifugal loop 14 and to a source 35 of a demulsifier. A conventional flow transmitter 36 senses the flow of the demulsifier in line 32 and provides a corresponding flow rate signal to flow controller 29.

In operation, the set point signal means 27 utilizes the difference in the watercuts between the two sample streams to adjust the set point of flow controller 29 which in turn controls valve 30 in accordance with the set point and the signal from flow transmitter 36.

The sample streams are joined together after the watercut testing and provided back to centrifugal loop 14 through a line 38 which enters centrifugal loop 14 downstream from sampling tubes 18 and 20.

Water cut monitor 25, shown in FIG. 2, includes a microwave transmitter 43 providing electromagnetic energy, hereinafter referred to as microwave energy, at a microwave frequency. Transmitter 43 is low powered and may use a microwave gun source. Transmitter 43 provides microwave energy to directional coupler 44. Directional coupler 44 provides microwave energy to a conventional type voltage controlled phase shifter 45 and to test apparatus 48. All conductance or carrying of microwave energy is accomplished by using conventional type waveguides and coaxial cables.

Test apparatus 48 is connected to sampling lines 18 and 20. The sample streams leave test apparatus 48 by way of lines 18 and 20 which join to form line 38. Apparatus 48 will be described in more detail hereinafter. Suffice to say at this point that microwave energy leaving test apparatus 48, hereinafter referred to as test microwave energy, is microwave energy that is either passed through the sample stream carried by line 18 or has passed through the sample stream carried by line 20. The test microwave energy is applied to a directional coupler 58. Directional coupler 58 provides the test microwave energy to a detector 62 and to a mixer 68. Detector 62 provides a signal E1 corresponding to the power of the test microwave energy.

As hereinafter explained, test apparatus 48 also provides a signal T corresponding to the temperature of the fluids being tested.

Voltage control phase shifter 45 provides microwave energy, hereinafter called the reference microwave energy, to mixer 68 which mixes the reference microwave energy and the test microwave energy to provide two electrical signals E2, E3, representative of the phases of the reference microwave energy and the test microwave energy, respectively.

A differential amplifier 70 provides an output signal E0 in accordance with the difference between signals E2 and E3.

Signal E0 is a function of the phase difference between the reference microwave energy and the test microwave energy and is provided to a feedback network 74. Feedback network 74 provides a signal C to voltage control phase shifter 45, controlling the phase of the reference microwave energy, and to a mini-computer means 80. Signal E0, and hence signal C, decreases in amplitude until there is substantially 90° phase difference between the reference microwave energy and the test microwave energy. Voltage control phase shifter 45 indicates the amount of phase shift required to eliminate the phase difference.

Signals E1 and T are also provided to mini-computer means 80 which contains within it memory means having data related to phase and power for various percentages of watercuts that could be encountered in the production stream. Phase Shifter 45 also provides an enable signal to computer means 80 allowing computer means 80 to utilize signals T, C and E1 to select the proper watercut value. Mini-computer means 80 provides signal EWC, corresponding to the selected watercut value, for the two stratified streams, to demulsifier source means 30.

Figure 2:
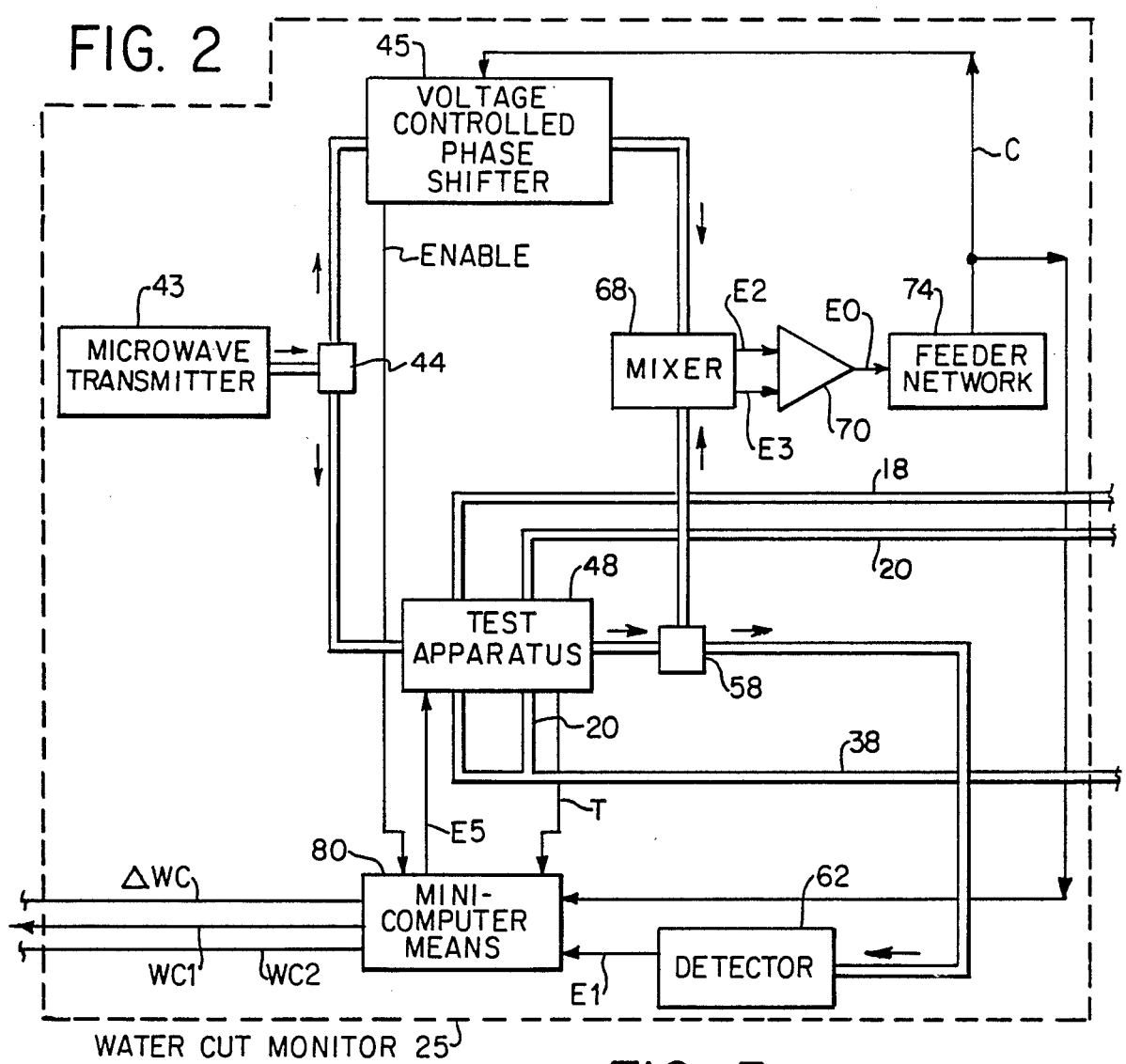
FIG. 2 is a detailed block diagram of the watercut monitor shown in FIG. 1.
Figure 3:
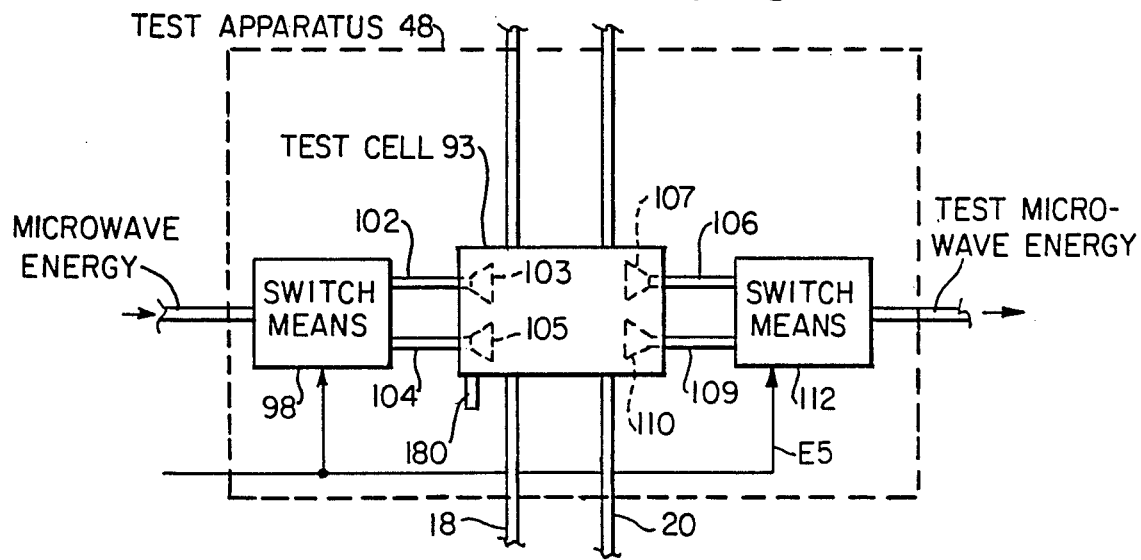
FIG. 3 is a detailed block diagram of the test apparatus shown in FIG. 2.

With reference to FIGS. 2 and 3, test apparatus 48 includes a test cell 93 receiving the stratified streams in lines 18 and 20. Test cell 93 will be described more fully hereinafter. Microwave energy from directional coupler 44 enters switch means 98 which provides microwave to test cell 93 through either a line 102 or a line 104. Line 102 provides the microwave to an antenna 103 which radiates the microwave energy into one stratified stream. Similarly, when microwave energy is provided by line 104, it is provided to an antenna 105. Antenna 105 radiates the microwave energy into the other stratified stream. Line 106 carries test microwave energy received by an antenna 107 after it has passed through the one stratified stream. Similarly, line 109 carries microwave energy received by an antenna 110 after it has passed through the other stratified stream. Switch means 112 receives the test microwave energy from either line 106 or line 107 and provides it to directional coupler 58. The stratified streams leave test cell 93 via lines 18 and 20.

Figure 4:
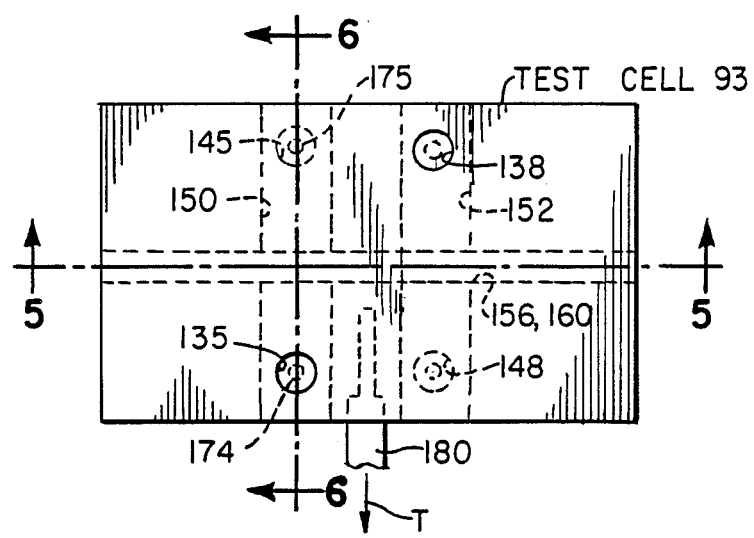
FIG. 4 is a drawing of the test cell shown in FIG. 3.

With reference to FIG. 4, there is shown test cell 93 having microwave entrance ports 135 and 138. On the other side of test cell 93 as represented by dash lines are microwave exit ports 145 and 148. Connecting microwave entrance port 135 and microwave exit port 145 is a microwave channel 150. Similarly a microwave channel 152 connects microwave entrance port 138 with microwave exit port 148.

Figure 5:
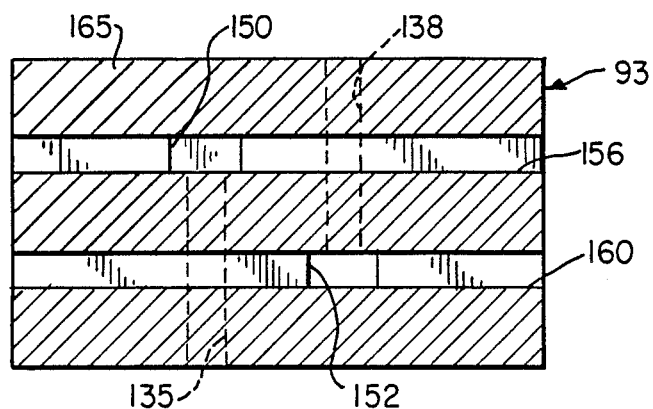
FIGS. 5 and 6 are cross sectional views of the test cell shown in FIG. 4.

Also shown in FIG. 4 are fluid channels 156 and 160. Since fluid channels 156 and 160 are in line in this view of test cell 93 only one set of dash lines represents them. This can seen better in FIG. 5 which has a cut away view of test cell 93 in the direction of the arrows 5—5. There is shown a body 165, which may be made of metal, having fluid channels 156 and 160 passing through it longitudinally and microwave channels 150 and 152 for the microwave energy cut transversely through it. It should be noted that channels 150 and 152 are shown as being offset from each other. However this offset, although preferred, is not necessary to the practice of the present invention.

It should also be noted that fluid channels 156, 160 have a rectangular cross-section so that the microwave energy that passes through the fluids, always has the same distance of passage.

Figure 6:
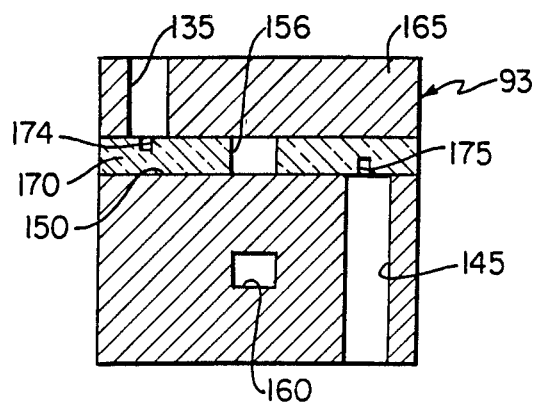

Referring to FIG. 6, there is a view of test cell 53 along the line 6—6 in the direction of 6—6, shown in FIG. 4. Channel 150 is filled with a solid material 170, such as high density teflon, that is conductive to microwave energy, except for that portion of channel 150 that forms a cross-section of fluid channel 156. Cut into body 165 is microwave entrance port 135. Further there is another chamber 174 which connects microwave entrance port 135 and enters into material 170 in channel 150. This is for the insertion of microwave antenna 103, which may be of the commercial type made by Omni Spectra, Part No. 2057-5134-02. Similarly, microwave exit port 145, for antenna 107, is shown with an additional chamber 175 which enters into material 170. Again this is for the purpose of monitoring the sample stream. Basically it is the same type of antenna as is entered with entrance port 135.

As can be seen, exit port 145 is longer than entrance port 135. The microwave energy when applied to the antenna 103 enters material 170 and is directed to cross channel 156 until it reaches the antenna 107 inserted in exit port 145.

Referring also to FIG. 3, lines 18 and 20 are connected in the conventional manner to channels 156, 160 so that the stratified stream in line 18 will flow through channel 156 in test cell 93 to line 18. Similarly, lines 20 and 20 are connected to fluid channel 160 in such a manner that the stratified stream in line 20 will enter fluid channel 160 and exit test cell 93 through line 20.

As can be seen in FIG. 4, a temperature sensor 170 which is a thermocouple, is inserted into a chamber cut into block 145 and thus reads the temperature of block 145 as the temperature of the stratified streams.

What is claimed is:

1. A system for controlling the addition of a demulsifier to a petroleum stream comprising:
   means receiving the petroleum stream for causing the petroleum stream to have a density gradient related to the water content of the petroleum stream,
   sampling means for sampling the petroleum stream along the density gradient to provide two sample streams,
   watercut means receiving the two sample streams for determining the watercut of each sample stream and providing at least one signal corresponding thereto, and
   source means responsive to at least one of the signals from the watercut means for providing the demulsifier to the petroleum stream upstream of the creation of the density gradient of the petroleum stream.

2. A system as described in claim 1 in which the source means includes:
   a source which provides the demulsifier, and
   control means connected to the watercut means and to the source for controlling the providing of the demulsifier from the source to the petroleum stream in accordance with the signal from the watercut means.

3. A system as described in claim 2 in which the control means includes:
   line means connected to the source for carrying the demulsifier from the source to the petroleum stream,
   valve means cooperating with the line means for controlling the flow of the demulsifier in the line means in accordance with a control signal,
   a flow transmitter senses the flow of the demulsifier in the line means and provides a corresponding flow signal,
   a flow controller, connected to the valve means and to the flow transmitter and having a set point provides the control signal to the valve means in accordance with the setting of the set point and the flow signal from the flow transmitter, and set point means connected to the watercut means and to the flow controller for adjusting the set point of the flow controller in accordance with the signal from the watercut means.

4. A system as described in claim 3 in which the signal provided by the watercut means to the set point means corresponds to the difference between the watercuts of the two sample streams.

5. A system as described in claim 1 in which the watercut means includes:
   test cell means connected to the sampling means for having the sample streams flowing through it,
   microwave means for transmitting microwave energy,
   first antenna means connected to the microwave means for transmitting microwave energy into on sample stream or the other sample stream,
   second antenna means for receiving microwave energy that has passed through the one sample stream or the other stream sample and providing the received microwave energy as test microwave energy,
   detector means connected to the second antenna means for detecting the power of the test microwave energy and providing a power signal corresponding thereto, and
   signal means connected to the second antenna means, to the source means and to the detector means for providing signals corresponding to watercuts of both sample streams and to the difference between the watercuts in accordance with the power signal and the phase difference between the transmitted microwave energy and the received microwave energy.

6. A system as described in claim 5 further comprising:
   means for sensing the temperature of the two sample streams and providing a temperature signal corresponding thereto, and
   wherein the signal means provides the signals corresponding to the watercuts and to the difference between the watercuts in accordance with the power signal, the phase difference between the transmitted energy and the received microwave energy and the temperature signal.

7. A system as described in claim 6 in which the test cell means includes:
   a body having two channels therein for fluid passage and two channels for microwave energy passage,
   means for receiving the sample streams and providing them to different fluid channels,
   means for allowing the sample streams to exit from the body; and wherein one fluid channel and one microwave channel intersect each other at right angles and the other fluid channel and the other microwave channel intersect each other at right angles.

8. A system as described in claim 7 in which each microwave channel contains a material, except for that portion of the microwave channel that crosses a fluid channel, that is impervious to fluids but permits passage of the microwave energy.

9. A system as described in claim 8 in which the first antenna means includes:
   first transmitter antenna means spatially arranged with one of the microwave channels for transmitting microwave energy into the one microwave channel,
   second transmitter antenna means spatially arranged with the other microwave channel for transmitting microwave energy into the other microwave channel, and
   first switch means connected to the source means and to the first and second transmitter antennas for providing the microwave energy transmitted by the source means to either the first transmitter antenna means or to the second transmitter antenna means; and
   the second antenna means includes:
   a first receiving antenna spatially arranged with the one microwave channel,
   a second receiving antenna spatially arranged with the other microwave channel,
   second switching means connected to the first and second receiving antenna and cooperating with the first switching means for passing microwave energy that has passed through a fluid channel and received by a receiving antenna to the detector means and to the indicator means.

10. A system as described in claim 9 in which the solid material in the microwave channel is Teflon.

11. A system as described in claim 6 in which the watercut means also provides signals representative of the watercuts of the sample streams.

12. A system as described in claim 11 further comprising:
   read out means connected to the signal means for providing read outs of the watercuts and the difference between watercuts in accordance with the signals from the signal means.

13. A method for controlling the addition of a demulsifier to a petroleum stream comprising the steps of:
   affecting the petroleum stream to establish a density gradient,
   sampling the petroleum stream at different points along the density gradient to provide two sample streams,
   determining the watercut of each sample stream,
   providing at least one output signal corresponding to the determined watercuts, and
   providing the demulsifier from a source to the petroleum stream 2-upstream of the affecting of the petroleum stream in response to the output signal.

14. A method as described in claim 13 in which the demulsifier providing step includes:
   carrying the demulsifier from the source to the petroleum stream via line means,
   controlling the flow of the demulsifier in the line means in accordance with a control signal with a valve,
   sensing the flow of the demulsifier in the line means providing a flow signal corresponding to the sensed demulsifier flow,
   a flow controller, connected to the valve means and to the flow transmitter and having a set point
   providing the control signal to the valve means with a flow controller in accordance with the setting of a set point of the flow controller and the flow signal, and
   adjusting the set point of the flow controller in accordance with the output signal.

15. A method as described in claim 14 in which the output signal corresponds to the difference between the watercuts of the two sample streams.

16. A method as described in claim 15 in which the output signal step includes:

providing output signals indicative of the values of the watercuts of the sample streams.

17. A method as described in claim 16 further comprising the step of:
providing read outs of the watercuts and the difference between watercuts in accordance with the output signals.

* * * * *